United States Patent [19]
Nettamo et al.

[11] Patent Number: 5,369,987
[45] Date of Patent: Dec. 6, 1994

[54] SEALLESS CONSISTENCY TRANSMITTER

[76] Inventors: Kari Nettamo; Markku Mustonen, both of 3730 Willow Mill Dr., Lawrenceville, Ga. 30244

[21] Appl. No.: 899,725

[22] Filed: Jun. 17, 1992

[51] Int. Cl.⁵ ............................ G01N 11/16; G01N 11/14
[52] U.S. Cl. ................................. 73/54.23; 73/54.38; 73/54.24
[58] Field of Search ............... 73/54.23, 54.24, 54.38

[56] References Cited
U.S. PATENT DOCUMENTS

| | | | |
|---|---|---|---|
| 3,364,730 | 1/1968 | Wall | 73/54.24 |
| 4,062,226 | 12/1977 | Hietala | 73/54.23 |
| 4,148,215 | 4/1979 | Hofsetter, Jr. | 73/54.23 |
| 4,757,708 | 7/1988 | Hietaranta | 73/54.23 |

*Primary Examiner*—Robert J. Warden
*Assistant Examiner*—T. A. Trembley
*Attorney, Agent, or Firm*—James B. Middleton

[57] ABSTRACT

A consistency transmitter for a pipe carrying a pulp mixture has a sensor blade within the pipe and an arm outside the pipe. The sensor blade is carried by a diaphragm, so the diaphragm is flexed in response to motion of the sensor blade. The arm is connected to the diaphragm so the arm is moved in response to movement of the sensor blade. A blade extends across the diaphragm to constrain the diaphragm to motion in one direction. A probe detects motion of the arm, the circuitry being remote from the probe and connected to the probe by a cable.

9 Claims, 1 Drawing Sheet

U.S. Patent     Dec. 6, 1994     5,369,987
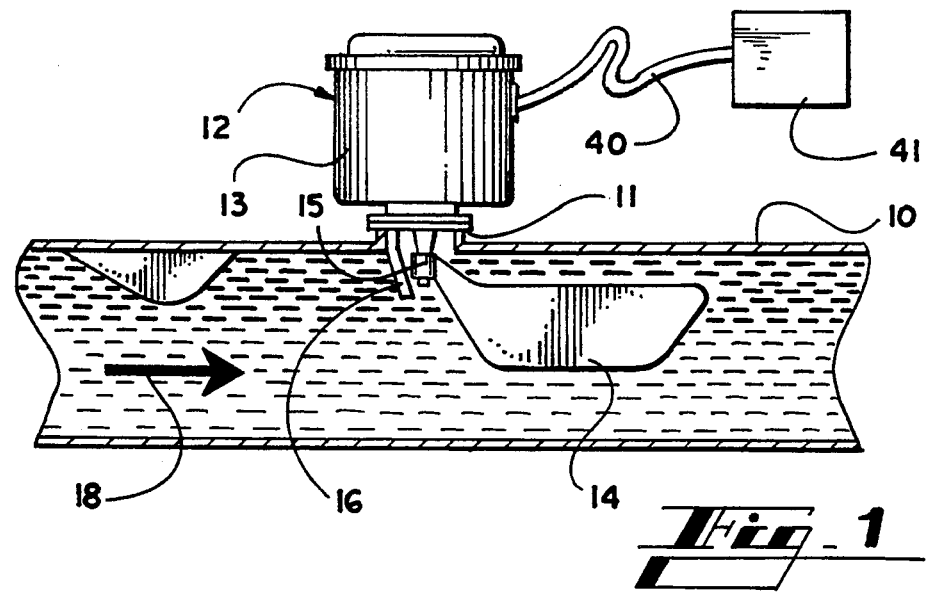
_Fig_1
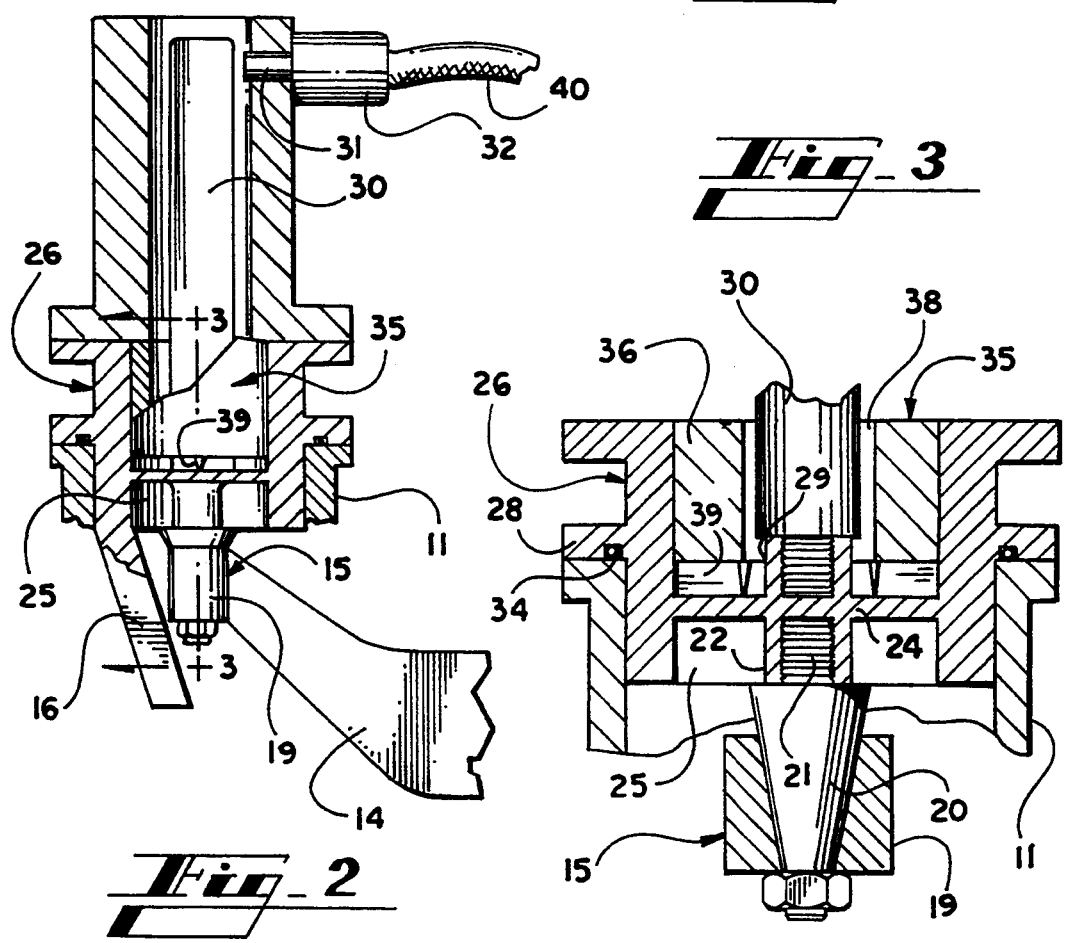
_Fig_2
_Fig_3

SEALLESS CONSISTENCY TRANSMITTER

FIELD OF THE INVENTION

This invention relates generally to measuring systems, and is more particularly concerned with a sealless transmitter for pulp consistency measurements.

BACKGROUND OF THE INVENTION

Consistency measuring apparatus is well known in the paper processing industry, the apparatus being designed to detect the consistency of the pulp flowing through a pipe, and to provide some indication of that consistency. Such consistency measuring apparatus generally includes a sensor blade disposed in the pipe so the blade is subjected to the pulp as the pulp flows through the pipe. The sensor blade is carried by an arm, the arm being pivotally mounted with respect to the pipe, so motion of the arm can be detected to give an indication of the consistency. Since the arm is pivotal with respect to the pipe, it will be understood that flexible sealing means is used to allow the motion while retaining the liquid within the pipe.

The sealing means in the prior art apparatus is a source of some problems. It will be understood that small rocks or other hard substances are sometimes in the pipe line, and these hard substances can hit the flexible seal and damage the seal. Also, heat and time will eventually cause damage to the seal so the seal will leak. The electronic measuring apparatus is normally in a single housing with the end of the arm of the sensor plate. so leakage may destroy all the electronic measuring apparatus.

The conventional technique for detecting motion of the arm comprises a variable capacitor. One group of plates is fixed with respect to the pipe, and the other group of plates is movable by the arm carrying the sensor plate. As a result, when the sensor arm moves, the group of capacitor plates moves, changing the capacitance of the variable capacitor. Well known electronic circuitry can then be used to detect the change in capacitance, and to calibrate the change in terms of consistency. Because of this technique, it will be understood that the electronics must be mounted at the consistency measuring device, and cannot be removed to a more distant, safe, location. Also, the device must always be returned to "zero" before making subsequent measurements.

SUMMARY OF THE INVENTION

The present invention provides a consistency transmitter wherein a sensor blade is disposed in a pipe so the blade is subjected to fluid flowing through the pipe. A shaft carrying the blade is fixed to a diaphragm, the diaphragm being integral with a plug fixed to the pipe. A second shaft is on the opposite side of the diaphragm, outside the pipe. Motion of the sensor blade is transmitted by the diaphragm to an arm, and means is provided to detect motion of the arm.

In the preferred form of the invention, the diaphragm is provided with diametrical supporting means to limit motion of the diaphragm so the arm will move in only one plane. It is contemplated that proximity sensing means will then sense motion of the arm, and the electronic circuitry can be placed remotely from the consistency transmitter. Further, any change in proximity can be detected without returning to a "zero" point after each measurement.

BRIEF DESCRIPTION OF THE DRAWINGS

These and other features and advantages of the present invention will become apparent from consideration of the following specification when taken in conjunction with the accompanying drawings in which:

FIG. 1 is a side elevational view of a consistency transmitter made in accordance with the present invention, and showing the pipe in cross-section;

FIG. 2 is an enlarged, diametrical cross-sectional view of the device shown in FIG. 1; and, FIG. 3 is a cross-sectional view taken substantially along the line 3—3 in FIG. 2.

DETAILED DESCRIPTION OF THE EMBODIMENT

Referring now more particularly to the drawings, and to that embodiment of the invention here presented by way of illustration, FIG. 1 shows a pipe 10 carrying pulp for making paper, or similar material. The pipe 10 has a T-member fixed thereto, as by welding or the like, so the T-member is effectively a part of the pipe 10. This T-member 11, then, receives the consistency transmitter of the present invention, generally designated at 12.

There is a sensor blade 14 disposed within the pipe 10, the blade 14 being supported from an arm 15. Adjacent to the arm 15 is a protection pin 16 which will be discussed in more detail hereinafter. Those skilled in the art will realize that the apparatus described so far is well known in the art. A sensor blade is placed in a pipe, the blade being carried by a shaft. The shaft is then carried by a transmitter housing. As the pulp mixture, known in the trade as "process", moves through the pipe 10 in the direction of the arrow 18 there will be a certain drag on the sensor blade, urging the blade 14 in the direction of process flow. The blade 14 is not free to move along the pipe 10, but the blade is capable of pivotal motion, so the blade 14 will pivot, moving the arm 15. One can then detect the motion of the arm 15 and determine the consistency of the process. The protector pin 16 will divert rock and other hard material away from the sensor blade 14 to prevent damage to the blade, and false readings due to heavy particles within the process.

The prior art arm 15 extends from within the pipe 10, through an appropriate seal or the like, and into the housing 13 for the indicating apparatus. In the present invention, however, there is no such communication.

Looking at FIGS. 2 and 3 of the drawings, it can be seen that the arm 15 comprises a sleeve 19 formed integrally with the blade 14. The sleeve 19 is received over a stub shaft 20 having a threaded end 21. The threaded end 21 is threadedly received by a threaded cup 22 which is formed integrally with a diaphragm 24.

The diaphragm 24 extends transversely across a bore 25 of a fitting 26. The fitting 26 is generally cylindrical and is received within the T-member 11. The fitting 26 will be fixed to the T-member 11 by appropriate fastening means, such as a plurality of screws through the flange 28.

The opposite side of the diaphragm 24 has another threaded cup 29 arranged coaxially with the cup 22. The threaded cud 29 receives the threaded end of the arm 30. As is shown in FIG. 2, as the arm 30 moves, the outer end of the arm 30 will move towards and away from the probe 31 having a coil 32. The probe 31 acts as a proximity device for determining motion of the arm 30 with respect to the probe 31. Though many arrangements may be utilized, the preferred form of the invention includes an arm 30 of aluminum or other paramagnetic material, and a coil 32 having a current flowing therethrough. The reverse current (back e.m.f.) generated in the coil 32 is easily measurable to give an indication of the proximity of the arm 30 to the probe 31.

With the foregoing description in mind, it will be seen that the process is contained within the pipe 10, and can flow into the T-member 11 and into the bore 25 of the fitting 26. It will be noted, however, that the diaphragm provides a closure that will prevent the process from passing beyond the diaphragm. Further, the diaphragm 24 will not allow leakage even after long use, because, in the preferred embodiment of the invention, the diaphragm 24 is formed integrally with the fitting 26.

If process is to leak from the pipe 10 at the T-member 11, the only possible path is between the fitting 26 and the T-member 11. To prevent such leakage, there is an O-ring 34. In any event, leakage would not be able to flow into the electronic apparatus for sensing the position of the arm 30.

For the sensor blade 14 to move, and cause motion of the arm 30, the diaphragm 24 must flex due to forces on the blade 14. It is important, however, that the diaphragm 24 will flex to allow motion of the arm 30 in only one plane. To accomplish this restriction of motion, there is a fulcrum member 35 received in the bore 25 on the same side of the diaphragm 24 as the arm 30. The fulcrum member 35 comprises a cylindrical body 36 having an axial hole 38 to receive the arm 30. On the bottom of the body 36, in contact with the diaphragm 24, there are blades 39. As is best seen in FIG. 2 of the drawings, the blades 39 have sharp edges resting against the diaphragm 24. The two blades are arranged to contact the diaphragm 24 along a diameter thereof. Thus, the blades 39 will support the diaphragm 24 and prevent motion in one direction; but, the diaphragm 24 can easily move, pivoting on the sharp edges of the blades 39 to allow motion in a direction perpendicular to the blades. As a result, the arm 30 is constrained to move in a single plane, which is towards and away from the probe 31.

The means for detecting and measuring the motion of the arm 30 includes the probe 31 and the coil 32, and additional electronic circuitry connected to the coil 32 by the cable 40. Because of this, the box 41 containing the circuitry can be located wherever desired. The circuitry 41 can be away from the process line, away from vibration, heat and other deleterious aspects of the usual paper processing environment.

It will therefore be seen that the device of the present invention provides a diaphragm that absolutely isolates the consistency sensing blade 14 in the process stream from the measuring apparatus and circuitry outside the process stream. The diaphragm is constrained to allow motion of the measuring arm in only one plane, and the use of proximity detecting means renders measurement simple, and allows the electronics to be mounted remotely from the process stream. While one form of proximity sensor has been described herein, it will be understood that other arrangements will be equally acceptable.

It will therefore be understood by those skilled in the art that the particular embodiment of the invention here presented is by way of illustration only, and is meant to be in no way restrictive; therefore, numerous changes and modifications may be made, and the full use of equivalents resorted to, without departing from the spirit or scope of the invention as outlined in the appended claims.

We claim:

1. In a consistency transmitter for a pipe line, comprising a pipe having a fluid flowing therethrough, a sensor blade disposed within said pipe and constructed to move pivotally in response to fluid flow, and means outside said pipe for detecting movement of said sensor blade, the improvement comprising a fitting within an opening in said pipe and sealed with respect to said opening, said fitting defining a bore therein, a diaphragm integral with said fitting and extending across said bore and closing said bore, said diaphragm having an inside surface in communication with the inside of said pipe and an outside surface opposite said inside surface, means fixed to said diaphragm for supporting said sensor blade from said inside surface of said diaphragm, and means fixed to said diaphragm for supporting said means outside said pipe for detecting movement of said sensor blade from said outside surface of said diaphragm, said diaphragm being flexed in response to pivotal movement of said sensor.

2. In a consistency transmitter as claimed in claim 1, said means for supporting said sensor blade including an arm fixed to said diaphragm, said sensor blade being carried by said arm.

3. In a consistency transmitter as claimed in claim 2, said sensor blade including a sleeve for fixing said sensor blade to said diaphragm, said sleeve being receivable over said arm.

4. In a consistency transmitter as claimed in claim 3, the further improvement including a threaded cup on said inside surface of said diaphragm, said arm being threadedly engaged with said threaded cup.

5. In a consistency transmitter as claimed in claim 1, said means outside said pipe for detecting movement comprising an arm fixed to said diaphragm, said means for supporting said means outside said pipe including a second threaded cup on said outside surface of said diaphragm.

6. In a consistency transmitter as claimed in claim 5, said means for supporting said sensor blade including an arm fixed to said diaphragm, said sensor blade being carried by said arm.

7. In a consistency transmitter as claimed in claim 6, the further improvement including a threaded cup on said inside surface of said diaphragm, said arm being threadedly engaged with said threaded cup.

8. In a consistency transmitter as claimed in claim 1, the further improvement including a fulcrum member adjacent to said outside surface of said diaphragm, said fulcrum member including a blade extending diametrically of said diaphragm in engagement with said outside surface.

9. In a consistency transmitter as claimed in claim 8, said fulcrum member further including a body received within said fitting, said blade being fixed to said body and extending diametrically thereof.

* * * * *